(12) United States Patent
Allef et al.

(10) Patent No.: US 8,466,097 B2
(45) Date of Patent: Jun. 18, 2013

(54) ABRASIVE AGENT BASED ON NATURAL RAW INGREDIENTS, HAVING PROPERTIES IMPROVING RHEOLOGY

(75) Inventors: Petra Allef, Essen (DE); Marcel Veeger, Goch (DE); Wolfgang Roecher, Kempen (DE); Susann Wiechers, Essen (DE); Andreas Landgraf, Essen (DE)

(73) Assignee: Evonik Stockhausen GmbH, Krefeld (DE)

( * ) Notice: Subject to any disclaimer, the term of this patent is extended or adjusted under 35 U.S.C. 154(b) by 0 days.

(21) Appl. No.: 13/501,251

(22) PCT Filed: Oct. 5, 2010

(86) PCT No.: PCT/EP2010/064777
§ 371 (c)(1),
(2), (4) Date: Apr. 11, 2012

(87) PCT Pub. No.: WO2011/051083
PCT Pub. Date: May 5, 2011

(65) Prior Publication Data
US 2012/0202730 A1 Aug. 9, 2012

(30) Foreign Application Priority Data
Nov. 2, 2009 (DE) .......................... 10 2009 046 272

(51) Int. Cl.
*C11D 3/14* (2006.01)

(52) U.S. Cl.
USPC ........... 510/139; 510/119; 510/130; 510/136; 510/137; 510/138; 510/462

(58) Field of Classification Search
USPC ................. 510/119, 130, 136, 137, 138, 139, 510/462
See application file for complete search history.

(56) References Cited

U.S. PATENT DOCUMENTS

| | | | |
|---|---|---|---|
| 4,279,890 A * | 7/1981 | Harris et al. ..................... 424/69 |
| 4,407,789 A | 10/1983 | Eigen et al. | |
| 5,830,445 A * | 11/1998 | Bouillon et al. ................. 424/69 |
| 5,871,756 A | 2/1999 | Jeffcoat et al. | |
| 6,235,296 B1 * | 5/2001 | Daniel et al. ................... 424/401 |
| 6,376,438 B1 * | 4/2002 | Rosenberger et al. ........ 510/139 |
| 6,432,430 B1 | 8/2002 | Fitzjarrell | |
| 6,471,983 B1 | 10/2002 | Veeger et al. | |
| 6,489,275 B1 * | 12/2002 | Veeger et al. ................. 510/127 |
| 7,241,452 B2 | 7/2007 | Veeger et al. | |
| 7,851,511 B2 | 12/2010 | Allef et al. | |
| 7,906,664 B2 | 3/2011 | Allef et al. | |
| 7,910,119 B2 | 3/2011 | Allef et al. | |
| 2004/0170592 A1 | 9/2004 | Veeger et al. | |
| 2005/0026798 A1 | 2/2005 | Hollander | |
| 2007/0041927 A1 * | 2/2007 | Blaeser et al. ............. 424/70.27 |
| 2007/0292583 A1 | 12/2007 | Haynes et al. | |
| 2008/0152781 A1 | 6/2008 | Dreese | |
| 2008/0248144 A1 * | 10/2008 | Guenter et al. ................ 424/776 |
| 2008/0305056 A1 | 12/2008 | Jenni et al. | |
| 2009/0238935 A1 | 9/2009 | Haynes et al. | |
| 2009/0318570 A1 | 12/2009 | Veeger et al. | |
| 2010/0210499 A1 | 8/2010 | Allef et al. | |
| 2011/0021398 A1 * | 1/2011 | Allef et al. ..................... 510/138 |
| 2011/0046034 A1 * | 2/2011 | Stolz et al. .................... 510/130 |

FOREIGN PATENT DOCUMENTS

| | | |
|---|---|---|
| DE | 103 29 933 | 6/2005 |
| DE | 10 2005 054 976 | 5/2007 |
| EP | 1 136 063 | 9/2001 |
| GB | 103 699 | 2/1917 |
| GB | 452 115 | 8/1936 |
| WO | 92 09265 | 6/1992 |

OTHER PUBLICATIONS

International Search Report Issued Apr. 11, 2012 in PCT/EP10/64777 Filed Oct. 5, 2010.

* cited by examiner

*Primary Examiner* — Charles Boyer
(74) *Attorney, Agent, or Firm* — Oblon, Spivak, McClelland, Maier & Neustadt, L.L.P.

(57) ABSTRACT

The invention relates to flours of plant components, wherein a solution of 10 ml water and 1 ml of an aqueous methylene blue solution of 0.1 wt % brought into contact with 1 g of the flour, comprising an extinction at a wavelength of 660 nm to <1, to a method for producing said flours, products comprising said flours, and the use of the flours for producing skin and hand cleaning agents, surface cleansers, or peeling agents, and the use of the products for cleaning skin, hands, and surfaces.

12 Claims, No Drawings

3
ABRASIVE AGENT BASED ON NATURAL RAW INGREDIENTS, HAVING PROPERTIES IMPROVING RHEOLOGY

The invention relates to abrasive agents (abrasives), cosmetic products, in particular skin and hand cleansers, which comprise these abrasives, and their use for removing external soilings.

An essential constituent of cosmetic products, in particular cleansing and treatment compositions, is the abrasive agent, which has the task of aiding, in a mechanical way, the cleaning effect of washing-active and/or surfactant-like components.

The prior art describes numerous inorganic and organic materials which can be used in cleaning preparations as mechanical cleaning and treatment agents, in particular in hand cleansers or in so-called peeling creams and special cleansing gels. They serve here to remove the upper, dead skin cells or skin contaminants, for example on the face or on other parts of the body.

Of particular interest here are natural abrasives, such as e.g. washed and ground shells of walnuts and also ground apricot kernels or olive kernels, which, on account of their hardness and particle size, are suitable for superficial skin cleansing. Such natural abrasives have a gentle, very good cleaning effect without scratching the skin.

EP 0 559 696 describes a method for producing material treated with a bleach, in particular hydrogen peroxide, in fine distribution from natural shells and/or kernels, and describes the use of the bleached and low-germ abrasive obtained in this way in cosmetic products.

Since the bleaching of the natural kernel and shell flours has to be carried out in hydrous suspension, large amounts of waste liquors are also produced, as the extensive practice of this method has shown. Moreover, stabilizers and reducing agents and/or oxidizing agents are also used in the process; being additional raw materials, these naturally make the method more expensive compared to a possible method in which such stabilizers and/or reducing agents and/or oxidizing agents could be dispensed with.

To avoid such waste liquors, EP 1 136 063 A2 proposes a bleaching method in which, in a "dry" process, peracids are sprayed onto the natural flour, which can be obtained as biological material from a large number of plant materials, and are intended to bring about a lightening. The mixture of this biological material with the bleach should comprise no more than 60% by weight of water, with a post-ripening process starting after the mixing operation. After 10 days, the peroxide formed during the method should no longer be detectable in the product obtained.

DE 103 05 959 describes a method, the bleaching result of which with regard to germ content, odor and color, not only leads to abrasives which are comparable to or better, in their profile of properties, than the abrasives obtained by the method described in EP 0 559 696 B1 which, when used in cosmetic cleansers at the lowest possible concentration and/or with the complete omission of lightening substances, produce optically light and cosmetically acceptable products. In the aforementioned method, natural kernels, shells, fruit husks and/or seeds are ground to give a flour of defined particle size. The flour obtained is then treated in aqueous suspension with 1.0 to 10.0% by weight of a bleaching agent, based on the total batch amount. Here, the bleaching agent is added in two steps, where, in the first step, after adding from 20 to 40% by weight of the bleaching agent, based on the total use amount of the bleaching agent, a pH range from 3 to 5 is obtained.

DE 10 2005 054 976 describes a method for producing an abrasive substance, where natural kernels, shells, fruit husks and/or seeds are ground to give a flour of defined particle size, the flour is treated in aqueous suspension with at least one bleaching agent, the addition of the amount of bleaching agent taking place in two steps, in which, in the first step, at least 40% by weight to 90% by weight of the total amount of bleaching agent is added and the flour is degerminated in the acidic medium and, in the second step, the lightening and defatting of the flour is brought about by the simultaneous dosing of the remainder of the bleaching agent with an alkali solution in an alkaline medium. In this document, moreover, it is indicated that the fat content of the abrasives has a not insignificant influence on the properties, in particular the viscosity of the cosmetics produced using the bleached abrasives, preferably skin and hand cleansers, such as e.g. rough hand cleansers.

The degermination e.g. of spices and spice flours by means of irradiation with e.g. ionizing rays, is known from the food industry.

The irradiated flours of the prior art have the disadvantage that, when they are incorporated into cosmetic products, after storage for several weeks, a considerable decrease in the viscosity of the products is observed, which makes it necessary to use viscosity stabilizers or to add agents that increase viscosity. The bleached flours of the prior art have the disadvantage that, during their production, large amounts of water and chemicals are used which have to be disposed of, in some cases with a high degree of complexity.

The object of the present invention was to provide a flour which does not have one or more disadvantages of the prior art and which, in particular, has less of an influence on the viscosity and/or long-term viscosity of the products produced using this flour than the irradiated flours known from the prior art.

Surprisingly, it has been found that flours which, in the form of a dispersion of 1 g of the flour, 10 ml of water and 1 ml of a 0.1% strength by weight aqueous methylene blue solution, have an extinction at a wavelength of 660 nm of <1, have a considerably lesser influence on the (long-term viscosity) viscosity of the products produced therewith, than conventional flours.

The present invention therefore provides flours, cosmetic products and their use as described in the claims.

The flours according to the invention have the advantage that, when they are used for producing cosmetic products, the viscosity of the products which is obtained directly after production changes only a little or not at all.

Products which lose their viscosity considerably after production have to be produced with a high starting viscosity in order to avoid instabilities upon storage. These highly viscous products, however, can only be poured slowly, if at all, which is undesired from the point of view of production efficiency.

The preferably used flours which are obtained by a heat treatment moreover have the advantage that they are not only germ-free, but are sterile, i.e. are also free from spores.

The present invention is described below by way of example without intending to limit the invention to these exemplary embodiments. Where ranges, general formulae or compound classes are given below, then these are intended to encompass not only the corresponding ranges or groups of compounds that are mentioned explicitly, but also all part ranges and part groups of compounds which can be obtained by removing individual values (ranges) or compounds. Where documents are cited within the context of the present description, then their content, in particular the aspects specified in the citation, is deemed, in its entirety, as belonging to the disclosure of the present invention. Unless stated otherwise, all % data below are data in % by mass and all average-value data are number-average data.

The flour according to the invention of plant constituents (plant flour) is characterized in that a solution of 10 ml of water and 1 ml of a 0.1% strength by weight aqueous methylene blue solution which is brought into contact with 1 g of the flour has an extinction at a wavelength of 660 nm of <1, preferably between 0.01 and 1, preferably between 0.05 and 0.5 and particularly preferably between 0.1 and 0.3.

The measurement of the extinction can take place in such a way that 1 g of the flour to be measured is stirred with 10 ml of water and 1 ml of a 0.1% strength by weight aqueous methylene blue solution at 300 rpm for 10 minutes and the resulting mixture is filtered over a 1 μm glass frit. The stirring can be carried out e.g. using a Multipoint HP 15 electronic stirrer from Variomag. The glass frit used can be e.g. a 1 μm glass frit of the type CHROMAFIL® GF-100/25 from Macherey-Nagel GmbH & Co KG. On the filtrate obtained, a CADAS 200 spectrophotometer from Hach Lange GmbH is then used to measure the extinction at a wavelength of 660 nm against deionized water as standard. Cuvettes which can be used are those with a path length of 10 mm, e.g. those of the type Makro PS Cat. No. 634-2500 from VWR International GmbH.

In principle, the flour according to the invention can be obtained from all suitable plant constituents, such as e.g. bark, stem, fruit or leaves. Preferably, flours according to the invention are those which from the stem/stalk or the bark of a plant, such as e.g. wood or straw flours, or from fruits or parts thereof, such as e.g. fruit husks, peels, stalks, spindles or seeds.

Flours preferred according to the invention are those which are based on natural shell or kernel flours, such as e.g. nut shell flours, such as e.g. walnut shell flour or hazelnut shell flour, olive kernel flour, apricot kernel flour, almond shell flour, peach kernel flour, cherry kernel flour, plum kernel flour, palm kernel flour, coconut shell flour, coconut flour, jojoba fruit flour, macadamia nut (shell) flour, pistachio and pine shell flours and stone fruit kernel shell flours or mixtures thereof. According to the invention, a particularly preferred natural shell or kernel flour is walnut shell flour or corn cob spindle flour.

The flour according to the invention preferably has an average (number-average) particle size of from 50 to 2000 μm, preferably from 70 to 1000 μm and particularly preferably from 80 to 200 μm. Preferably, the flour has a mass fraction with a particle size of <100 μm of at most 15% by weight, preferably at most 10% by weight, and a mass fraction with a particle size of 100 to 200 μm of at least 85% by weight, preferably at least 90% by weight (determined using a shaking sieve in accordance with DIN 4188).

The bulk density of the flours according to the invention is preferably from 250 to 750 g/l, preferably from 350 to 650 g/l and particularly preferably from 450 to 600 g/l (determined in accordance with DIN 53466).

The flour according to the invention is preferably low-germ or germ-free. Low-germ is understood as meaning flours with a total germ count of $<10^3$ CFU/g, preferably <250 CFU/g, preferably $<10^2$ CFU/g (determined in accordance with European Pharmacopeia, 5th edition, 6th supplement, chapter 2.6.12).

The flours can be obtained e.g. by treating the plant parts with the comminution apparatuses or mills known in the prior art, as have been listed e.g. in EP 0 559 696, in particular impact mills with pendulum or plate impacter, passage roll mills, hammer impact or pin-type mills, optionally with classification units, such as e.g. Condux mills etc. In order to obtain a defined particle size of the flours, these can be classified in a manner known per se after the comminution/grinding e.g. by means of sieving.

Flour according to the invention preferably has a fat content, determined in accordance with DGF Standard Method B-I 5 (87), (DGF Standard Methods German standard methods for investigating fats, fat products, surfactants and related substances, Wissenschaftliche Verlagsgesellschaft Stuttgart), of less than 1% by weight, preferably less than 0.5, preferably less than 0.3% by weight. The low-fat flour has the advantage that it can be incorporated particularly well into hydrophilic matrices and it has only a slight influence, if any, on the viscosity of the formula.

The flour according to the invention is preferably heat-treated and/or bleached, particularly preferably heat-treated and not bleached. Within the context of the present invention, bleaching is understood as meaning the treatment of the flour with chemical oxidizing agents. The flour according to the invention is preferably not radiation-treated or at least not exclusively radiation-treated.

The flours according to the invention can be obtained in various ways. Preferably, flours according to the invention are obtained by subjecting an untreated flour to a heat treatment and/or a bleaching treatment, preferably to a heat treatment and no bleaching treatment, and the parameters of the treatment are preferably chosen such that a flour is obtained which is characterized in that a solution of 10 ml of water and 1 ml of a 0.1% strength by weight aqueous methylene blue solution which is brought into contact with 1 g of the flour, has an extinction at a wavelength of 660 nm of less than (<) 1.

If the treatment of flour is carried out as heat treatment, then this can take place by any method known in the prior art. The heat treatment can take place e.g. by treating with hot air, infrared radiation, vapor, preferably alcohol and/or water, electrothermal treatment, such as e.g. ohmic, inductive, microwave, high-frequency treatment or by means of high-pressure methods. Preferably, the heat treatment takes place by treatment of the flours with vapor, in particular water vapor, preferably saturated water vapor (saturated steam).

The treatment according to the invention of the flours preferably takes place such that the flour to be treated is exposed preferably for 30 sec to 60 min, preferably for 1 to 20 min and particularly preferably for 2 to 10 min, to a temperature of preferably 70 to 150° C., preferably 70 to 130° C., particularly preferably from 100 to 130° C. and very particularly preferably from 100 to 125° C. It may be advantageous if the heat treatment, in particular that with saturated steam, is carried out at a superatmospheric pressure, preferably at a superatmospheric pressure of at least 1.5 bar, preferably at a superatmospheric pressure of from 2 to 3 bar.

Irrespective of the treatment method, the treated flour can preferably be subjected to a drying process. The storage stability of the flour can be increased in this way. For the drying, methods known in the prior art can be used. Preferably, the drying takes place by applying a subatmospheric pressure, preferably ca. 50 mbar in the case of simultaneous thermal treatment, preferably at a temperature of greater than 25° C. to less than 130° C. During the drying, the product is preferably cooled to 30 to 50° C. The drying preferably takes place such that a residual moisture of 20% by weight, preferably 10% by weight, is not exceeded. Preferably, the residual moisture is <10% by weight, in particular less than or equal to 9.5% by weight. The residual moisture or the water content can be determined in accordance with DIN 51777.

The treatment, preferred according to the invention, of the flour with vapor, preferably saturated stream, preferably takes place by the following process: the flour to be treated is introduced into a pressurized chamber. The chamber is preheated to a temperature of 100° C. or more, preferably from 100 to 125° C. Preferably, the chamber is evacuated, in particular to a pressure of ca. 50 mbar. Then, water vapor, preferably saturated steam (i.e. water-saturated vapor) is introduced up to preferably 1 to 3 bar above atmospheric pressure. The temperature is preferably held for 2 to 10 min. The chamber is then evacuated again to ca. 50 mbar. As a result of the evacuation, a dried product is obtained. After this treatment, the resulting product has a residual temperature of 25 to 45° C., preferably 35° C.

If the treatment according to the invention takes place using bleaching agent(s), this can in principle take place as in the prior art, in particular as described in DE 10 2005 054 976 and DE 103 29 933. However, the heat treatment is preferred over the bleaching since the former produces much less waste water and dispenses with the use of oxidizing agents.

Bleaches which can be used are all compounds which ensure an irreversible destruction of the bacteria in the flours, where the bleached flours during the bleach treatment according to the invention are chemically modified only insignificantly, if at not, meaning that they can be used as abrasives in cosmetic products. Such bleaching agents are e.g. so-called oxidizing bleaching agents, as are described, for example, in Ullmanns Encyclopedia of Industrial Chemistry, 4th edition, vol. 8, pages 589 to 595. Preference is given to inorganic and organic peroxides, such as e.g. hydrogen peroxide, sodium peroxide, barium peroxide or peroxycarboxylic acids, in particular peroxyformic acid, peroxyacetic acid and peroxypropionic acid etc., which can also be prepared in situ and used according to the invention in a known manner for the person skilled in the art. The aforementioned compounds can be used on their own or else as a mixture of at least two of these compounds in the method according to the invention. According to the invention, the bleaching agent to be used is preferably aqueous hydrogen peroxide solution.

The preferably heat-treated flour according to the invention and/or the flour obtained by the method according to the invention can be used e.g. for producing products, preferably cosmetic products, such as e.g. skin or hand cleansers, peeling compositions, or surface cleaners, in particular in household and industrial surface cleaners, in particular as an abrasive. In particular, use in solvent-free or solvent-containing hand washing pastes, in anhydrous skin cleaners and in peeling creams is preferred.

Preferred products, in particular cosmetic products according to the present invention, are those which have a flour according to the invention or a flour produced according to the invention. Preferably, a product according to the invention comprises from 1 to 30% by weight, preferably from 5 to 25% by weight and particularly preferably from 5 to 20% by weight, based on the total composition, of flour according to the invention.

The skin and hand cleansers can be e.g. those as are known from DE 43 35933 A1, WO 99/06021, DE 197 48 921 A1, EP 1 152 051 A2 or DE 199 16 036 A1.

Preferred products according to the invention, in particular cosmetic products, preferably skin and hand cleanses, are those which have a content of at least 0.1% by weight, preferably from 0.5 to 10% by weight, preferably from 1 to 5% by weight, of at least one hydrophilic emollient with an HLB value of ≧8, preferably an HLB value of ≧10, with sorbitan esters being particularly preferred as hydrophilic emollients.

These have the advantage that they are skin and/or hand cleansers which ensure a very good cleaning effect even for the most stubborn of skin soilings, coupled with very good skin compatibility. In particular, the skin and hand cleansers produce a very good skin feel even during washing, this very good skin impression, on account of the low degree of drying-out of the skin also remaining perceptible to the user for some time after washing, and thus increasing the acceptance by the user with regard to the use of rough hand cleaners.

For the preferred product according to the invention, in particular cosmetic product, as well as the presence of the flour according to the invention, also the presence of a hydrophilic emollient which has an HLB value of ≧8 is essential to the invention. The HLB value is a measure of the water solubility or oil solubility of predominantly nonionic surfactants and emulsifiers, for example in cosmetic products, and thus describes the hydrophilic part and the lipophilic part of a chemical compound. Thus, an HLB value of 0 corresponds to a purely lipophilic compound. By contrast, a chemical compound with an HLB value of 20 has only hydrophilic parts. Thus, water-in-oil emulsions are assigned HLB values between 3 and 8, whereas oil-in-water emulsions have HLB values between 8 and 18, and detergents have HLB values between 13 and 15 (see also RÖMPP—Chemistry Lexicon, 10th edition, page 1764, keywords: HLB system, HLB value—and literature cited therein). For the invention present here, emollients with an HLB value between 1 and 8 are referred as to hydrophobic, and those with an HLB value ≧8 are preferred to as hydrophilic.

According to the invention, the (cosmetic) products according to the invention, in particular skin and hand cleansers, preferably have a content, in each case based on the total composition of the cleanser, of the components a.) at least 0.1% by weight of at least one hydrophilic emollient, preferably a polyol ester, b.) 2 to 40% by weight of at least one surfactant selected from the group of the fatty alcohol ethoxylates, fatty alcohol ether sulfates and salts of sulfated and/or sulfonated fatty acids, c.) 30 to 90% by weight of water, d.) 0 to 30% by weight of one or more cleansing boosters selected from the group of the polyols, polyethers, polyphosphates and phosphates, e.) 1 to 30% by weight of one or more flours according to the invention (abrasives), f.) optionally one or more viscosity-forming agents, g.) optionally further cosmetic auxiliaries, additives and/or active ingredients, where the sum of components a.) to h.) gives 100% by weight.

The polyols esters to be used as component a.), which are to be regarded as hydrophilic emollient in the cosmetic products according to the invention, in particular skin and hand cleansers, may be, for example, partial glycerides, in particular polyglyceryl partial esters. According to the invention, preference is given to polyglyceryl partial esters of the general formula (I)

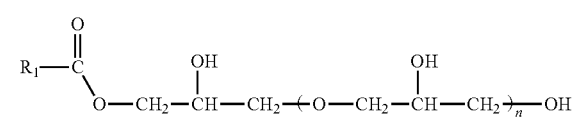

where
$R_1$=linear, branched or cyclic, saturated or unsaturated alkyl or alkenyl radical having
6 to 18 carbon atoms
n=integer from 1 to 9.

The linear, branched or cyclic, saturated or unsaturated alkyl or alkenyl radical $R_1$ has preferably 6 to 16 and particularly preferably 8 to 12 carbon atoms. The index n is preferably 1 to 5, preferably 2 to 3.

The polyglyceryl partial esters or polyglycerol fatty acid esters particularly preferred according to the invention are, for example, polyglyceryl-3-caprate or polyglyceryl-4-caprate, which are available from Evonik Goldschmidt GmBH under the name TEGOSOFT® PC31 and TEGOSOFT® PC41.

As hydrophilic emollient a.), however, it is also possible to use polyglycerol esters with a different structure, e.g. based on 1,2- or 1,3-linked polyglycerols, or polyglycol esters.

As hydrophilic emollients a.), it is likewise possible to use polyethylene glycol esters, such as e.g. PEG-7 glyceryl cocoate, which is available from Croda Chemicals Europe Ltd. under the name Glycerox HE. As hydrophilic emollients, the component a.) in the cosmetic products according to the invention can also comprise polysaccharide esters and/or polysaccharide ethers and/or polysaccharide glycosides with an HLB $\geq 8$, preferably $\geq 10$. Preference is given to using sucrose esters, as can be acquired for example from Evonik Goldschmidt GmbH under the names TEGOSOFT® LSE 65 K and TEGOSOFT® LSE 65 K Soft, and also sorbitan esters, as can be acquired for example from Evonik Goldschmidt GmbH under the name Antil® soft SC (sorbitan sesquicaprylate).

The fraction of component a.) in the cosmetic products according to the invention is preferably up to 10% by weight, preferably 0.1 to 7.5% by weight, particularly preferably 0.5 to 5% by weight, based on the composition of the cosmetic product. The hydrophilic emollients can be present on their own or in multiples as component a.) in the skin and hand cleansers according to the invention.

In the cosmetic products according to the invention, 2 to 40% by weight, preferably 3 to 30% by weight and particularly preferably 5 to 20% by weight of surfactants b.), preferably fatty alcohols ethoxylates, based on the composition of the cosmetic product, are present.

The fatty alcohol ethoxylates that can be used as component b.) preferably have the general formula (II)

$$R^2-O-(CH_2-CH_2-O)_m H \qquad (II)$$

where
$R^2$=saturated, unsaturated, branched or unbranched alkyl radical, preferably having 6 to 18, preferably having 10 to 16 and particularly preferably having 11 to 14 carbon atoms, and m=integer from 1 to 11, preferably 3 to 10 and preferably 5 to 7.

In a preferred embodiment, the cosmetic products according to the invention have 5 to 10% by weight, based on the composition of the product, of laureth-6 as fatty alcohol ethoxylate.

The fatty alcohol ether sulfates which can be used as component b.) preferably have the formula (III)

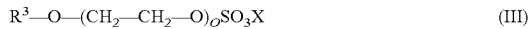

$$R^3-O-(CH_2-CH_2-O)_o SO_3 X \qquad (III)$$

where $R^3$=a $C_8$-$C_{18}$, preferably $C_{11}$-$C_{14}$ saturated or unsaturated, branched or unbranched alkyl radical and o=an integer from 1 to 6, preferably 1 to 4, and $X=Na^+$, $NH_4^+$ or $Mg^{2+}$, where sodium lauryl ether sulfate (where $R^3=C_{12}$, o=2-3 and $X=Na^+$) is particularly preferred.

According to the invention, the salts of sulfated and/or sulfonated fatty acids of component b.) used are preferably alkali metal or alkaline earth metal salts of preferably $C_8$-$C_{30}$, preferably $C_{10}$-$C_{22}$ fatty acids, particularly preferably castor oil sulfates, in particular $Na^+$ or $NH_4^+$ sulfates. Such castor oil sulfonates are available, for example, under the name Monobrilliantöl® (Stockhausen GmbH, Krefeld).

The (cosmetic) products according to the invention, in particular skin and hand cleansers, preferably comprise 30 to 90% by weight, preferably 40 to 80% by weight and particularly preferably 45 to 75% by weight, based on the composition of the cleanser, of water as component c.).

Although the (cosmetic) products according to the invention, in particular as skin and hand cleansers, exhibit a very good cleaning effect, such that the addition of cleaning boosters can per se be dispensed with, the skin and hand cleansers can optionally comprise cleaning boosters from the class of polyols, polyethers, polyphosphates and phosphates as component d.) for certain cleaning applications. Particular preference is given here to polyethers which are formed from the polymerization of ethylene glycol and 3 to 20 units, preferably 4 to 10 units. Preference is given to PEG-8, as can be acquired, for example, from Ineos under the names PEG 400.

The products according to the invention, in particular skin and hand cleansers, can comprise solvents for boosting the cleaning. Preferably, carboxylic acid esters of the type methyl oleate and carboxylic acid diesters of the type dimethyl adipate, dimethyl glutarate, dimethyl succinate (DBE) and di-n-butyl adipate or diisopropyl adipate can be present as solvents.

Moreover, the products according to the invention, in particular skin and hand cleansers, can optionally comprise one or more viscosity-forming agents, such as, for example, organophilic and/or hydrophilic sheet silicates, as component f.), in particular bentonites, polysaccharides, such as e.g. cellulose, guar flour and/or xanthans, modified polysaccharides, preferably cellulose ethers, carboxyalkylcellulose and/or hydroxyalkylcelluloses, preferably hydroxyethylcellulose and/or inorganic electrolytes, preferably sodium chloride and/or magnesium sulfate. According to the invention, particular preference as component f.) is given to carboxymethylcelluloses (e.g. Walocel CRT—Wolff Cellulosics, Walsrode), which, moreover, bring about the very good foam-stabilizing effect when using the skin and hand cleansers according to the invention. The skin and hand cleansers according to the invention particularly advantageously comprise 0.1 to 1.5% by weight of component f.), based on the total composition of the cleanser.

Furthermore, the products according to the invention, in particular skin and hand cleansers, can optionally comprise further cosmetic auxiliaries, additives and/or active ingredients, for example pH regulators, stabilizers, preferably cetearyl alcohol and/or hydrogenated castor oils, such as e.g. trihydroxystearin, fragrances, preservatives, preferably organic acids and antioxidants, such as, e.g. vitamin E acetate, as component g.). Preferably, it is also possible to use oily or aqueous care components, such as, for example, bisabolol, aloe vera, panthenol, sodium PCA, jojoba oil, creatine etc., in order to reinforce the care effect.

The (cosmetic) products according to the invention, in particular skin and hand cleansers, in particular rough hand cleansers, can be produced in the customary manner by means of known devices in a batch or continuous procedure, the skin and hand cleansers preferably being obtained as creamy compositions or as flowable viscous pastes. Suitable devices are heatable vessels with stirrer, continuous mixers such as extruders and dispersers.

The skin and hand cleansers according to the invention exhibit a very good cleaning effect, coupled with very good skin compatibility and low drying-out of the skin. It is particularly advantageous that the skin and hand cleansers according to the invention produce a very good skin feel during washing. The skin feel after washing is also considerably more pleasant after some time on account of the lower drying-out of the skin.

The cosmetic product according to the invention is preferably a skin or hand cleanser, in particular a rough hand cleanser.

The (cosmetic) product according to the invention can be used e.g. for cleaning the hands or the skin, as peeling composition, or as industrial and household surface cleaner.

The invention is described in more detail by reference to the examples below without limiting it to these embodiments.

EXAMPLES

Example 1

Production of Treated Flours

Example 1a

Production of a Heat-Treated Flour

A walnut shell flour acquired from Bardon Ethablisements under the name Vegetale C 180 was introduced in a pressurized chamber. The chamber was preheated to a temperature of 100° C. and then the chamber was evacuated to a pressure of ca. 50 mbar. Then, water-saturated vapor was introduced at 1 bar above atmospheric pressure. The temperature was held for 2 min. The chamber was then evacuated again to ca. 50 mbar. As a result of the evacuation, a dried heat-treated flour was obtained.

Example 1b

Production of an Irradiated Flour

A walnut shell flour acquired from Bardon Ethabilisements under the name Vegetale C 180 was irradiated at Isotron in Marseille with a cobalt 60 emitter up to a radiation intensity of 8 KGray in the inside of the 1000 kg big bag.

Example 1c

Producing a Bleached Flour

A walnut shell flour acquired from Bardon Ethabilisements under the name Vegetale C 180 was bleached in accordance with the example in DE 10 2005 054 976.

Example 2

Determination of the Extinction

The extinction was measured by stirring 1 g of the flour to be measured with 10 ml of water and 1 ml of a 0.1% strength by weight aqueous methylene blue solution with a Multipoint HP 15 electronic stirrer from Variomag at 300 rpm for 10 minutes and filtering the resulting mixture over a 1 μm glass frit of the type CHROMAFIL® GF-100/25 from Macherey-Nagel GmbH & Co KG. On the filtrate obtained, a CADAS 200 spectrophotometer from Hach Lange GmbH was then used to measure the extinction at a wavelength of 660 nm against deionized water as standard. The cuvettes used were of the type Makro PS Cat. No. 634-2500 with a path length of 10 mm from VWR International GmbH.

The measurement results are summarized in table 1.

TABLE 1

| Extinctions of the investigated flours | |
|---|---|
| | Extinction |
| Flour as in example 1a | 0.158 |
| Flour as in example 1b | 1.069 |
| Flour as in example 1c | 0.089 |

Example 3

Determination of the HLB Value

The HLB value was determined by preparing a 5% strength dispersion/solution of the substance to be tested, here the hydrophilic emollient, in water, and determining the water solubility. The assessment was carried out visually: clouding, solubility, degree of dispersion. The HLB value was determined by means of comparison with solutions of emulsifiers whose HLB values are known. The ascertained HLB values are given in table 2.

TABLE 2

| Ascertained HLB values: | | |
|---|---|---|
| | HLB value | Abbreviation |
| TEGOSOFT ® PC 31 | 14 | PC31 |
| TEGOSOFT ® PC 41 | 16 | |
| Antil ® Soft SC | 10 | Antil Soft |

Example 4

Production of Cleaning Formulations

Skin and hand cleansers as per the compositions given in tables 3a to 3f were produced by stirring together all of the components using the cold-cold procedure customary in cosmetics at room temperature. For the compositions according to table 3f, commercially available flours from plant constituents as supplied by Impag were used. In each case, formulations without flour, with flour according to the invention and with flour not according to the invention were produced. The formulations were characterized with regard to their viscosity.

TABLE 3a

| Composition of the cleaning formulations in % by wt. | | | | | | |
|---|---|---|---|---|---|---|
| Ingredients according to INCI nomenclature | 4a | 4b | 4c | 4d | 4e | 4f |
| AQUA(WATER) | 71.86 | 72.79 | 72.86 | 72.79 | 71.86 | 72.79 |
| LAURETH-6 | 6.00 | 6.00 | 6.00 | 6.00 | 6.00 | 6.00 |
| SODIUM LAURETH SULFATE | 2.60 | 2.60 | 2.60 | 2.60 | 2.60 | 2.60 |
| SULFATED CASTOR OIL | 2.73 | 2.73 | 2.73 | 2.73 | 2.73 | 2.73 |
| DISODIUM LAURETH SULFOSUCCINATE | 1.98 | 1.98 | 1.98 | 1.98 | 1.98 | 1.98 |

TABLE 3a-continued

Composition of the cleaning formulations in % by wt.

| Ingredients according to INCI nomenclature | 4a | 4b | 4c | 4d | 4e | 4f |
|---|---|---|---|---|---|---|
| Flour as in example 1a | | | 5.70 | 5.70 | | |
| Flour as in example 1b | | | | | 5.70 | 5.70 |
| Flour as in example 1c | 5.70 | 5.70 | | | | |
| PEG-4 RAPESEEDAMIDE | 1.86 | 0.93 | 1.86 | 0.93 | 1.86 | 0.93 |
| POLYGLYCERYL-3 CAPRATE (Tegosoft ® PC 31) | 1.20 | | 1.20 | | 1.20 | |
| PPG-11 Stearyl Ether (Varonic APS) | 0.30 | | 0.30 | | 0.30 | |
| Sorbitan Sesquicaprylate (Antil ® soft SC) | | 1.50 | | 1.50 | | 1.50 |
| CARBOXYMETHYL CELLULOSE | 0.70 | 0.70 | 0.70 | 0.70 | 0.70 | 0.70 |
| SODIUM CHLORIDE | 1.92 | 1.92 | 1.92 | 1.92 | 1.92 | 1.92 |
| Oleic acid | 1.10 | 1.10 | 1.10 | 1.10 | 1.10 | 1.10 |
| SODIUM BENZOATE | q.s. | q.s. | q.s. | q.s. | q.s. | q.s. |
| POTASSIUM SORBATE | q.s. | q.s. | q.s. | q.s. | q.s. | q.s. |
| PARFUM (FRAGRANCE) | q.s. | q.s. | q.s. | q.s. | q.s. | q.s. |
| CITRIC ACID | q.s. | q.s. | q.s. | q.s. | q.s. | q.s. |
| CI 77891 (titanium dioxide) | 0.50 | 0.50 | 0.50 | 0.50 | 0.50 | 0.50 |
| Viscosity decrease in mPas | 3000 | 1000 | 9000 | 6000 | 36 000 | 24 000 |

TABLE 3b

Composition of the cleaning formulations in % by wt.

| Ingredients according to INCI nomenclature | 4g | 4h | 4i | 4j | 4k | 4l |
|---|---|---|---|---|---|---|
| AQUA(WATER) | 67.14 | 66.74 | 67.14 | 66.74 | 67.14 | 66.74 |
| LAURETH-6 | 6.00 | 6.00 | 6.00 | 6.00 | 6.00 | 6.00 |
| SODIUM LAURETH SULFATE | 3.38 | 3.38 | 3.38 | 3.38 | 3.38 | 3.38 |
| SULFATED CASTOR OIL | 2.73 | 2.73 | 2.73 | 2.73 | 2.73 | 2.73 |
| DISODIUM LAURETH SULFOSUCCINATE | 1.98 | 1.98 | 1.98 | 1.98 | 1.98 | 1.98 |
| Flour as in example 1a | | | 11.40 | 11.40 | | |
| Flour as in example 1b | | | | | 11.40 | 11.40 |
| Flour as in example 1c | 11.40 | 11.40 | | | | |
| POLYGLYCERYL-3 CAPRATE (Tegosoft ® PC 31) | 1.20 | | 1.20 | | 1.20 | |
| PPG-11 Stearyl Ether (Varonic APS) | 0.30 | | 0.30 | | 0.30 | |
| Sorbitan Sesquicaprylate (Antil ® soft SC) | | 1.50 | | 1.50 | | 1.50 |
| CARBOXYMETHYL CELLULOSE | 0.70 | 0.70 | 0.70 | 0.70 | 0.70 | 0.70 |
| XANTHAN GUM | | 0.40 | | 0.40 | | 0.40 |
| SODIUM CHLORIDE | 1.92 | 1.92 | 1.92 | 1.92 | 1.92 | 1.92 |
| Oleic acid | 1.20 | 1.20 | 1.20 | 1.20 | 1.20 | 1.20 |
| SODIUM BENZOATE | q.s. | q.s. | q.s. | q.s. | q.s. | q.s. |
| POTASSIUM SORBATE | q.s. | q.s. | q.s. | q.s. | q.s. | q.s. |
| PARFUM (FRAGRANCE) | q.s. | q.s. | q.s. | q.s. | q.s. | q.s. |
| CITRIC ACID | q.s. | q.s. | q.s. | q.s. | q.s. | q.s. |
| CI 77891 (titanium dioxide) | 0.50 | 0.50 | 0.50 | 0.50 | 0.50 | 0.50 |
| Viscosity decrease in mPas | 4000 | 8000 | 6000 | 15 000 | 24 000 | 42 000 |

TABLE 3c

Composition of the cleaning formulations in % by wt.

| Ingredients according to INCI nomenclature | 4m | 4n | 4o | 4p | 4q | 4r |
|---|---|---|---|---|---|---|
| AQUA(WATER) | 58.05 | 57.85 | 58.05 | 57.85 | 58.05 | 57.85 |
| LAURETH-6 | 9.50 | 9.50 | 9.50 | 9.50 | 9.50 | 9.50 |
| SODIUM LAURETH SULFATE | 3.12 | 3.12 | 3.12 | 3.12 | 3.12 | 3.12 |
| SULFATED CASTOR OIL | 2.73 | 2.73 | 2.73 | 2.73 | 2.73 | 2.73 |
| DISODIUM LAURETH SULFOSUCCINATE | 2.97 | 2.97 | 2.97 | 2.97 | 2.97 | 2.97 |
| Flour as in example 1a | | | 16.15 | 16.15 | | |
| Flour as in example 1b | | | | | 16.15 | 16.15 |
| Flour as in example 1c | 16.15 | 16.15 | | | | |
| POLYGLYCERYL-3 CAPRATE (Tegosoft ® PC 31) | 1.20 | | 1.20 | | 1.20 | |
| PPG-11 Stearyl Ether (Varonic APS) | 0.30 | | 0.30 | | 0.30 | |
| Sorbitan Sesquicaprylate (Antil ® soft SC) | | 1.50 | | 1.50 | | 1.50 |
| CARBOXYMETHYL CELLULOSE | 0.70 | 0.70 | 0.70 | 0.70 | 0.70 | 0.70 |
| XANTHAN GUM | | 0.50 | | 0.50 | | 0.50 |
| SODIUM CHLORIDE | 2.13 | 2.13 | 2.13 | 2.13 | 2.13 | 2.13 |
| Oleic acid | 1.10 | 0.80 | 1.10 | 0.80 | 1.10 | 0.80 |
| SODIUM BENZOATE | q.s. | q.s. | q.s. | q.s. | q.s. | q.s. |

TABLE 3c-continued

Composition of the cleaning formulations in % by wt.

| Ingredients according to INCI nomenclature | 4m | 4n | 4o | 4p | 4q | 4r |
|---|---|---|---|---|---|---|
| POTASSIUM SORBATE | q.s. | q.s. | q.s. | q.s. | q.s. | q.s. |
| PARFUM (FRAGRANCE) | q.s. | q.s. | q.s. | q.s. | q.s. | q.s. |
| CITRIC ACID | q.s. | q.s. | q.s. | q.s. | q.s. | q.s. |
| CI 77891 (titanium dioxide) | 0.50 | 0.50 | 0.50 | 0.50 | 0.50 | 0.50 |
| Viscosity decrease in mPas | 10 000 | 3000 | 15 000 | 4000 | 37 000 | 30 000 |

TABLE 3d

Composition of the cleaning formulations in % by wt.

| Ingredients according to INCI nomenclature | 4s | 4t | 4u | 4v |
|---|---|---|---|---|
| AQUA(WATER) | 66.99 | 66.99 | 67.74 | 67.74 |
| LAURETH-6 | 6.00 | 6.00 | 6.00 | 6.00 |
| SODIUM LAURETH SULFATE | 3.38 | 3.38 | 3.38 | 3.38 |
| SULFATED CASTOR OIL | 2.73 | 2.73 | 2.73 | 2.73 |
| DISODIUM LAURETH SULFOSUCCINATE | 1.98 | 1.98 | 1.98 | 1.98 |
| Flour as in example 1a | 12.00 | | 12.00 | |
| Flour as in example 1b | | 12.00 | | 12.00 |
| Lamesoft PO 65 (Coco-Glucoside (and) Glyceryl Oleate) | 2.25 | 2.25 | | |
| SUCROSE COCOATE | | | 1.50 | 1.50 |
| CARBOXYMETHYL CELLULOSE | 0.70 | 0.70 | 0.70 | 0.70 |
| XANTHAN GUM | 0.40 | 0.40 | 0.40 | 0.40 |
| SODIUM CHLORIDE | 1.92 | 1.92 | 1.92 | 1.92 |
| Oleic Acid | 1.20 | 1.20 | 1.20 | 1.20 |
| SODIUM BENZOATE | 0.60 | 0.60 | 0.60 | 0.60 |
| POTASSIUM SORBATE | 0.30 | 0.30 | 0.30 | 0.30 |
| PARFUM (FRAGRANCE) | 0.20 | 0.20 | 0.20 | 0.20 |
| CITRIC ACID | 0.45 | 0.45 | 0.45 | 0.45 |
| CI 77891 (titanium dioxide) | 0.50 | 0.50 | 0.50 | 0.50 |
| Viscosity decrease in mPas | 28 000 | 37 000 | 24 000 | 43 000 |

TABLE 3e

Composition of the cleaning formulations in % by wt.

| Ingredients according to INCI nomenclature | 4w | 4x | 4y | 4z |
|---|---|---|---|---|
| AQUA(WATER) | 71.94 | 71.94 | 72.69 | 72.69 |
| LAURETH-6 | 6.00 | 6.00 | 6.00 | 6.00 |
| SODIUM LAURETH SULFATE | 2.60 | 2.60 | 2.60 | 2.60 |
| SULFATED CASTOR OIL | 2.73 | 2.73 | 2.73 | 2.73 |
| DISODIUM LAURETH SULFOSUCCINATE | 1.98 | 1.98 | 1.98 | 1.98 |
| Flour as in example 1a | | 5.70 | | 5.70 |
| Flour as in example 1b | 5.70 | | 5.70 | |
| PEG-4 RAPESEEDAMIDE | 0.93 | 0.93 | 0.93 | 0.93 |
| Lamesoft PO 65 (Coco-Glucoside (and) Glyceryl Oleate) | 2.25 | 2.25 | | |
| SUCROSE COCOATE | | | 1.50 | 1.50 |
| CARBOXYMETHYL CELLULOSE | 0.70 | 0.70 | 0.70 | 0.70 |
| SODIUM CHLORIDE | 1.92 | 1.92 | 1.92 | 1.92 |
| Oleic acid | 1.10 | 1.20 | 1.20 | 1.20 |
| SODIUM BENZOATE | 0.60 | 0.60 | 0.60 | 0.60 |
| POTASSIUM SORBATE | 0.30 | 0.30 | 0.30 | 0.30 |
| PARFUM (FRAGRANCE) | 0.20 | 0.20 | 0.20 | 0.20 |
| CITRIC ACID | 0.45 | 0.45 | 0.45 | 0.45 |
| CI 77891 (titanium dioxide) | 0.50 | 0.50 | 0.50 | 0.50 |
| Viscosity decrease in mPas | 27 000 | 8000 | 26 000 | 7000 |

TABLE 3f

Composition of the cleaning formulations in % by wt.

| Ingredients according to INCI nomenclature | 5a | 5b | 5c | 5d | 5e | 5f |
|---|---|---|---|---|---|---|
| AQUA(WATER) | 67.74 | 67.74 | 67.74 | 67.74 | 67.74 | 67.74 |
| LAURETH-6 | 6.00 | 6.00 | 6.00 | 6.00 | 6.00 | 6.00 |
| SODIUM LAURETH SULFATE | 3.38 | 3.38 | 3.38 | 3.38 | 3.38 | 3.38 |
| SULFATED CASTOR OIL | 2.73 | 2.73 | 2.73 | 2.73 | 2.73 | 2.73 |
| DISODIUM LAURETH SULFOSUCCINATE | 1.98 | 1.98 | 1.98 | 1.98 | 1.98 | 1.98 |
| Guarana Green Exfoliator | 12.00 | | | | | |
| Karite (washed) | | 12.00 | | | | |
| Cranberry Bioexfoliator 200 | | | 12.00 | | | |
| Cranberry Exfoliator 500 | | | | 12.00 | | |
| Apricot Bioexfoliator 200 | | | | | 12.00 | |
| Apricot Bioexfoliator 1000 | | | | | | 12.00 |
| Apricot Exfoliator 500 | | | | | | |
| Sorbitan Sesquicaprylate (Antil ® soft SC) | 1.50 | 1.50 | 1.50 | 1.50 | 1.50 | 1.50 |
| CARBOXYMETHYL CELLULOSE | 0.70 | 0.70 | 0.70 | 0.70 | 0.70 | 0.70 |
| XANTHAN GUM | 0.40 | 0.40 | 0.40 | 0.40 | 0.40 | 0.40 |
| SODIUM CHLORIDE | 1.92 | 1.92 | 1.92 | 1.92 | 1.92 | 1.92 |
| Oleic acid | 1.20 | 1.20 | 1.20 | 1.20 | 1.20 | 1.20 |
| SODIUM BENZOATE | 0.60 | 0.60 | 0.60 | 0.60 | 0.60 | 0.60 |
| POTASSIUM SORBATE | 0.30 | 0.30 | 0.30 | 0.30 | 0.30 | 0.30 |
| PARFUM (FRAGRANCE) | 0.20 | 0.20 | 0.20 | 0.20 | 0.20 | 0.20 |
| CITRIC ACID | 0.45 | 0.45 | 0.45 | 0.45 | 0.45 | 0.45 |
| CI 77891 (titanium dioxide) | 0.50 | 0.50 | 0.50 | 0.50 | 0.50 | 0.50 |
| Viscosity decrease in mPas | 43 000 | 8000 | 10 000 | 2000 | 24 000 | 22 000 |
| Extinction | 2.297 | 0.703 | 0.538 | 0.951 | 2.506 | 3.480 |

Example 5

Determination of the Viscosity

To determine the viscosity, a Brookfield viscosimeter using the spindle type RV 6 was used. Measurement was carried out at a temperature of 20° C. The viscosities were determined directly after preparing the formulations given in examples 4 and 5. All formulations had a viscosity of from 40 000 to 45 000 mPas.

After storing the formulations for 3 months, the viscosity was determined again. The viscosity decrease for the formulations with the various flours can be found in the last lines of tables 3a to 3f.

The values relating to the viscosity decrease clearly reveal that the use of flour according to the invention leads to a significantly lower reduction in the viscosity than the use of irradiated flour.

As the last line of table 3 reveals, the viscosity decrease in the case of the use of flour not according to the invention is sometimes so great that the formulations become so thin-liquid that they are no longer suitable as hand/skin cleansers.

The invention claimed is:

1. A cosmetic product, comprising:
   a.) at least 0.1% by weight of a hydrophilic emollient having an a HLB value of $\geq 8$, based on a total mass of the product;
   b.) 2 to 40% by weight of at least one surfactant selected from the group consisting of a fatty alcohol ethoxylate, a fatty alcohol ether sulfate, a salt of sulfated fatty acid, and a salt of a sulfonated fatty acid;
   c.) 30 to 90% by weight of water;
   d.) 0 to 30% by weight of a cleansing booster selected from the group consisting of a polyol, a polyether, a polyphosphate, and a phosphate;
   e.) 1 to 30% by weight of an abrasive;
   f.) optionally a viscosity-forming agent;
   g.) optionally at least one component selected from the group consisting of a further cosmetic auxiliary, additive, and active ingredient; and
   h.) a heat-treated flour comprising plant constituents, wherein a solution of 10 ml of water and 1 ml of a 0.1% strength by weight aqueous methylene blue solution which is brought into contact with 1 g of the flour has an extinction at a wavelength of 660 nm of <1,
   wherein a sum of a.) to h.) is 100% by weight, and
   wherein the heat treated flour is made by a method comprising:
   heat treating the untreated flour with saturated steam, wherein the heat treatment period is from 1 to 20 min and the temperature is from 70 to 130° C., to obtain the flour.

2. The cosmetic product of claim 1, wherein a content of the flour in the product is from 1 to 30% by weight, based on the total mass of the product.

3. A skin or hand cleanser comprising the cosmetic product of claim 1.

4. A method for cleaning a surface, hands, or skin, the method comprising:
   applying the cosmetic product of claim 1 to a surface, hand, or skin in need thereof.

5. The cosmetic product of claim 1, wherein the flour is also bleached.

6. The cosmetic product of claim 1, wherein the flour has a fat content of less than 0.5% by weight, by DGF Standard Method B-1 5 (87).

7. The cosmetic product of claim 1, wherein the extinction at the wavelength of 660 nm is between 0.01 and 1.

8. The cosmetic product of claim 1, wherein the extinction at the wavelength of 660 nm is between 0.05 and 0.5.

9. The cosmetic product of claim 1, wherein the extinction at the wavelength of 660 nm is between 0.1 and 0.3.

10. The cosmetic product of claim 1, wherein the flour has an average particle size of from 50 to 2000 μm.

11. The cosmetic product of claim 1, wherein the flour has a fat content of less than 1% by weight, by DGF Standard Method B-1 5 (87).

12. The cosmetic product of claim 1, wherein the flour has a total germ count of $<10^3$ CFU/g.

* * * * *